United States Patent
Zelman et al.

(10) Patent No.: US 11,885,661 B2
(45) Date of Patent: Jan. 30, 2024

(54) DETECTING MATERIAL TYPE USING LOW-ENERGY SENSING

(71) Applicant: Wiliot, Ltd., Caesarea (IL)

(72) Inventors: Ido Zelman, Hod-Hasharon (IL); Matan Epstein, Tel-Aviv (IL); Shay Moshe, Pardes Hanna-Karkur (IL); Tsvika Rabkin, Pardes Hanna-Karkur (IL); David Lipshitz, Raanana (IL); Tal Szpruch, Kfar Saba (IL); Dotan Ziv, Tel-Aviv (IL); Alon Yehezkely, Haifa (IL)

(73) Assignee: WILIOT, LTD., Caesarea (IL)

( * ) Notice: Subject to any disclaimer, the term of this patent is extended or adjusted under 35 U.S.C. 154(b) by 0 days.

(21) Appl. No.: 17/171,795

(22) Filed: Feb. 9, 2021

(65) Prior Publication Data
US 2021/0255151 A1    Aug. 19, 2021

Related U.S. Application Data

(60) Provisional application No. 62/977,433, filed on Feb. 17, 2020.

(51) Int. Cl.
*G01F 23/28* (2006.01)
*G01F 23/284* (2006.01)
(Continued)

(52) U.S. Cl.
CPC .......... *G01F 23/284* (2013.01); *G01F 23/296* (2013.01); *G01N 29/348* (2013.01);
(Continued)

(58) Field of Classification Search
CPC .... G16H 20/17; G01F 23/296; G01N 29/348; G01N 29/4454; G01N 29/46; G06K 9/00536; G06K 9/6262
See application file for complete search history.

(56) References Cited

U.S. PATENT DOCUMENTS

| | | | |
|---|---|---|---|
| 7,775,083 B2 * | 8/2010 | Potyrailo | G01D 9/005 73/19.01 |
| 8,955,340 B2 | 2/2015 | Burke et al. | |

(Continued)

FOREIGN PATENT DOCUMENTS

| | | |
|---|---|---|
| WO | 2004081897 A2 | 9/2004 |
| WO | 2015128635 A1 | 9/2015 |
| WO | 2017175243 A1 | 10/2017 |

OTHER PUBLICATIONS

Alexander, et al., "Predicting Indoor Position Using Bluetooth Low Energy and Machine Learning", International Journal of Scientific & Technology Research, ISSN: 227708616, vol. 8, Issue 09, Sep. 2019.

(Continued)

*Primary Examiner* — Tarun Sinha
(74) *Attorney, Agent, or Firm* — M&B IP Analysts, LLC

(57) ABSTRACT

A system and method for detecting material type using low-energy sensing are disclosed. The method includes receiving frequency words from a tag attached to a container containing material, wherein the tag provides a low-energy sensing configured to transmit the frequency words; extracting at least a first data feature from the received frequency words, wherein the first data feature changes in response to a type of material in the container; classifying the extracted data feature to label a type of the material in the container; and sending a notification indicating the type of material in the container.

23 Claims, 9 Drawing Sheets

(51) Int. Cl.

| | |
|---|---|
| *G06N 20/00* | (2019.01) |
| *G16H 20/17* | (2018.01) |
| *G01F 23/296* | (2022.01) |
| *G01N 29/34* | (2006.01) |
| *G01N 29/44* | (2006.01) |
| *G01N 29/46* | (2006.01) |
| *G06F 18/21* | (2023.01) |

(52) U.S. Cl.
CPC ......... *G01N 29/4454* (2013.01); *G01N 29/46* (2013.01); *G06F 18/217* (2023.01); *G06N 20/00* (2019.01); *G16H 20/17* (2018.01); *G06F 2218/08* (2023.01); *G06F 2218/12* (2023.01)

(56) References Cited

U.S. PATENT DOCUMENTS

| | | | |
|---|---|---|---|
| 10,003,913 B2 | 6/2018 | Jin et al. | |
| 10,194,295 B2 | 1/2019 | Agostinelli et al. | |
| 10,275,710 B1 | 4/2019 | Teredesai et al. | |
| 10,282,967 B2 | 5/2019 | Law | |
| 10,467,501 B2 | 11/2019 | Sivakumar et al. | |
| 10,747,968 B2 | 8/2020 | Espinosa | |
| 11,494,569 B2 | 11/2022 | Espinosa | |
| 2005/0132796 A1* | 6/2005 | Brookner | H04B 5/0056 |
| | | | 73/290 R |
| 2014/0260623 A1* | 9/2014 | Salem | G01N 29/4472 |
| | | | 73/866 |
| 2017/0227673 A1 | 8/2017 | Venugopalan et al. | |
| 2018/0249735 A1 | 9/2018 | Espinosa | |
| 2020/0349328 A1 | 11/2020 | Espinosa | |

OTHER PUBLICATIONS

Stavrou, et al., "An Ensemble Filter for Indoor Positioning in a Retail Store Using Bluetooth Low Energy Beacons", MDPI Journal: Sensors, 2019.

International Search Report and Written Opinion of International Searching Authority for PCT/IB2021/051044, ISA/IL, Jerusalem, Israel, dated May 13, 2021.

International Search Report and Written Opinion of International Searching Authority for PCT/IB2021051045, ISA/IL, Jerusalem, Israel, dated May 20, 2021.

* cited by examiner

DETECTING MATERIAL TYPE USING LOW-ENERGY SENSING

CROSS-REFERENCE TO RELATED APPLICATIONS

This application claims the benefit of U.S. Provisional Application No. 62/977,433 filed on Feb. 17, 2020, the contents of which are hereby incorporated by reference.

TECHNICAL FIELD

The present disclosure relates generally to a system and method for detecting materials in containers, more particularly to detecting materials using low-energy sensing and machine learning.

BACKGROUND

There are many ways to detect materials, or the make-up of a material on a surface. For example, drawing from spectroscopy, reflection of light from a surface of a road may be detected, and the intensity of the detected light may be measured to indicate whether there is ice on a road surface. Other electromagnetic spectrums may be used to detect materials. For example, infrared signals reflected off of materials or surfaces may be detected, and based on heat signatures unique to materials, the material may be identified. Other modalities, including ultrasound, may be used.

However, the devices used under these modalities are often expensive and complicated and use signals that are incompatible with signals used among devices to communicate with each other. Also, these devices require a lot of energy to operate, further adding to their cost. In addition, such devices cannot detect materials in containers that are in transit. Further, it is difficult to make sense of the data collected, and a lot of resources need to be used to interpret the data.

Artificial Intelligence has been used to process massive amount of data. The machine learning processes involved with the application of artificial intelligence include supervised and unsupervised learning. In supervised learning, each data is classified to build a model. The classification is often performed manually by a classifier, which is time consuming, costly, and unwieldy when number of data collected is large.

With unsupervised learning, grouping or clustering of data as they are received is achieved without the need to classify each data. However, real-time inference of an event is difficult to achieve, as the discovery of hidden patterns in data without guidance of classified data is time consuming. Also, external evaluation is still required, which further adds to time and cost.

It would therefore be advantageous to provide a material sensing solution, and in particular for sensing solution for material in small containers that would overcome the challenges noted above.

SUMMARY

A summary of several example embodiments of the disclosure follows. This summary is provided for the convenience of the reader to provide a basic understanding of such embodiments and does not wholly define the breadth of the disclosure. This summary is not an extensive overview of all contemplated embodiments, and is intended to neither identify key or critical elements of all embodiments nor to delineate the scope of any or all aspects. Its sole purpose is to present some concepts of one or more embodiments in a simplified form as a prelude to the more detailed description that is presented later. For convenience, the term "some embodiments" or "certain embodiments" may be used herein to refer to a single embodiment or multiple embodiments of the disclosure.

Certain embodiments disclosed herein include a method for a method for detecting material type using low-energy sensing are disclosed. The method includes receiving frequency words from a tag attached to a container containing material, wherein the tag provides a low-energy sensing configured to transmit the frequency words; extracting at least a first data feature from the received frequency words, wherein the first data feature changes in response to a type of material in the container; classifying the extracted data feature to label a type of the material in the container; and sending a notification indicating the type of material in the container.

Certain embodiments disclosed herein include a system for developing a treatment plan using multi-stage machine learning. The system comprises a processing circuitry; and a memory, the memory containing instructions that, when executed by the processing circuitry, configure the system to: receive frequency words from a tag attached to a container containing material, wherein the tag provides a low-energy sensing configured to transmit the frequency words; extract at least a first data feature from the received frequency words, wherein the first data feature changes in response to a type of material in the container; classify the extracted data feature to label a type of the material in the container; and send a notification indicating the type of material in the container.

BRIEF DESCRIPTION OF THE DRAWINGS

The subject matter disclosed herein is particularly pointed out and distinctly claimed in the claims at the conclusion of the specification. The foregoing and other objects, features, and advantages of the disclosed embodiments will be apparent from the following detailed description taken in conjunction with the accompanying drawings.

DETAILED DESCRIPTION

Figure 1:
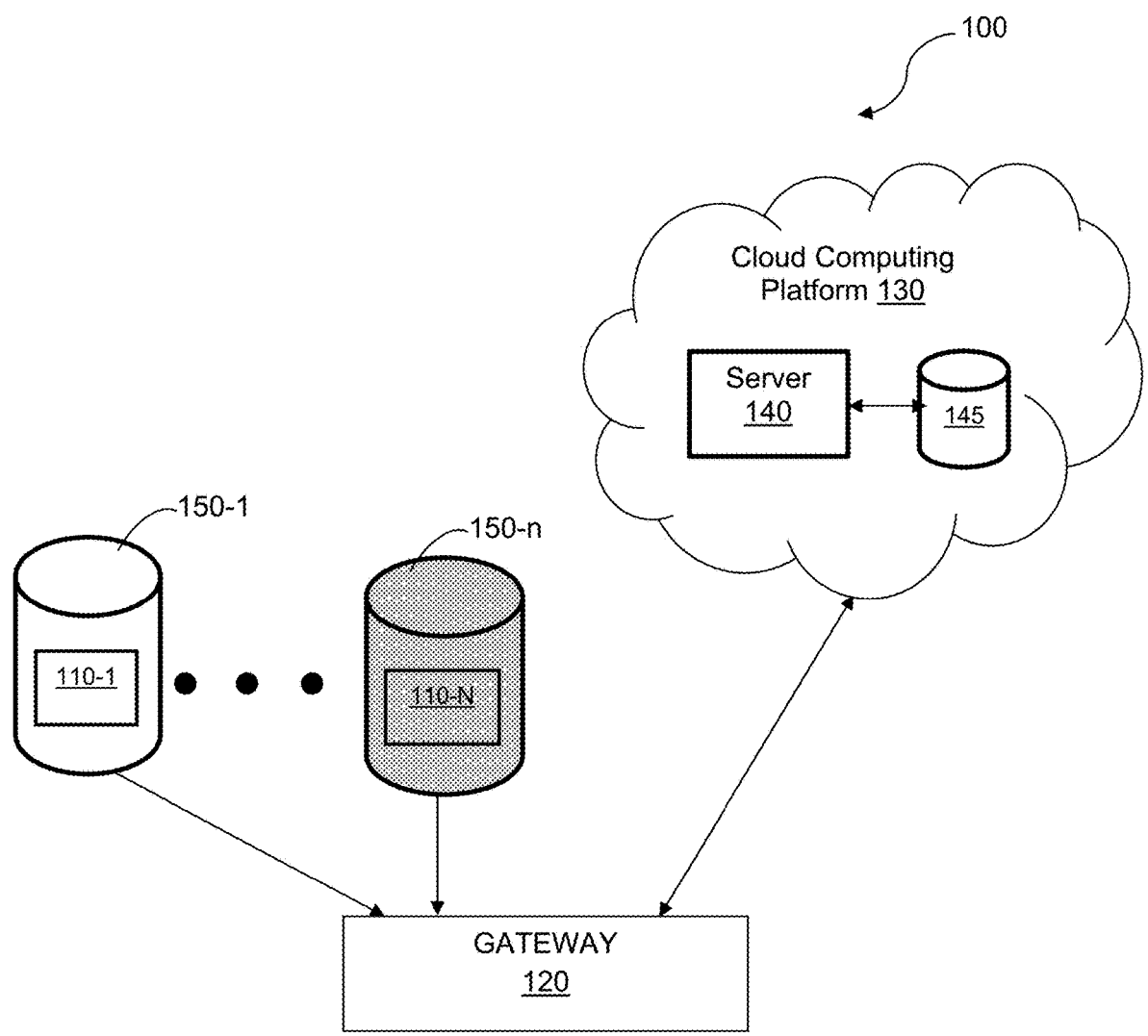
FIG. 1 is a schematic diagram of a secure low energy communication system utilized to describe the various embodiments.

It is important to note that the embodiments disclosed herein are only examples of the many advantageous uses of the innovative teachings herein. In general, statements made in the specification of the present application do not necessarily limit any of the various claimed embodiments. Moreover, some statements may apply to some inventive features but not to others. In general, unless otherwise indicated, singular elements may be in plural and vice versa with no loss of generality. In the drawings, like numerals refer to like parts through several views.

The various disclosed embodiments include a method and system for detecting a material type based on machine learning techniques and signals received from one or more IoT tags. A model is first developed based on collected signals received from the one or more IoT tags, whose values vary based on the material in a container on which an IoT tag is placed or attached to. The model is then applied one incoming signal to identify the material of the container and/or the surface that the container is placed. The signals in an embodiment include digital frequency words.

FIG. 1 is an example schematic diagram of a secure low energy communication system 100 utilized to describe the various embodiments. The system 100 includes a plurality of IoT tag 110-1 through 110-n (collectively referred to as a IoT tag 110 or IoT tags 110), a gateway 120, and a cloud computing platform 130. The system 100 also includes at least one server 140 that may be deployed in the cloud-based platform 130. The server 140 may be realized as a physical machine, a virtual machine, and the like.

In a preferred embodiment, the IoT tag 110 may be an Internet of Things (IoT) tag. In another embodiment, the IoT tag 110 is a battery-free IoT tag as discussed in FIG. 7. Also, communication among the IoT tag 110 and the gateway 120 may be performed using a low-energy communication protocol. The communication between the cloud computing platform 130 and the gateway 120 is over, for example, the Internet.

In an example embodiment, the low-energy communication protocol includes a Bluetooth Low Energy (BLE) protocol, which are short-wavelength radio waves operating at a range of about 2.40 to 2.485 MHz, and commonly used among portable wireless devices. The cloud computing platform 130 may include a public cloud, a private cloud, a hybrid cloud, or combination thereof.

The gateway 120 may be, but is not limited to, for example, a personal computer, a laptop, a tablet computer, a smartphone, a wearable computing device, or any other device capable of bridging between at least two different communication protocol, e.g., the BLE and HTTP. The gateway 120 may also communicate with a network (other than BLE networks), such networks include local area network (e.g., Wi-Fi), the Internet, and the like.

In an embodiment, the IoT tags 110 sense a particular RF activity relative to each other at a certain coordinate location. When a container 150 (e.g., container 150-1) is placed proximate to one of the IoT tags 110 (e.g., IoT tag 110-1) an interference to the ambient RF field causes a difference between the electrical properties of the material of the container and that of the ambient surroundings (e.g., air) which leads to a change in an RF value detected by the IoT tag 110-1 as a pick-up (i.e., interference) event. As will be explained in more detail below, the IoT tag 110-1 is configured to send the detected anomaly along with other information to the gateway 120. The gateway 120 is further configured to relay the combined information to the server 140. The server 140 is configured to perform further processing to identify the material make-up of a container 150-1.

It should be noted that the server 140 may be implemented as a physical machine, a virtual machine, or combination thereof. An example block diagram of the server 140 is provided in FIG. 8. In an embodiment, A database 145 may also deployed in the platform 130 and may be connected to the server 145. The database 145 may store events generate by server 140, identifiers (IDs) of IoT tags 110, and other signals.

In another embodiment, each IoT tag 110 is configured to send data packets to the gateway 120. The information in such data packets are later processed by the server 140 to detect the material of the item in the container 150 proximate to one of the IoT tags 110. For example, the container 150-1 may be a cup, a capsule, a box, a bottle, a vaccine vail, and the like. The material in the container 150 may be in a form of liquid, solid, or gas.

In an embodiment, a data packet, transmitted by the gateway 120, includes a digital frequency word and an Identification (ID) of the IoT tag 110. The frequency word is measured by an IoT tag 110 depending on a frequency calibration of the IoT tag 110. Any changes to the temperature in the ambient environment or changes of the material contained in the container placed among the IoT tags 110, will change the values detected among the IoT tags 110 from synchronization, thereby changing the value of the frequency word. In an example embodiment of the frequency calibration is discussed in more detail with reference to FIG. 7.

In an embodiment, the transmission frequency may be determined based on a Digitally Controlled Oscillator (DCO) signal. The DCO is utilized to calibrate an internal capacitor that changes its capacitance value to counteract the capacitance that a new material imposes, the DCO signal is a control signal of the DCO. That is, the IoT tag senses whether the transmission frequency is corrected, and if not to adjust the DCO to the main frequency of the transmission. When a different material is placed in the container, the tag has to recalibrate itself to the same transmission frequency by changing the capacitance value of its internal capacitor. In an embodiment, the transmission frequency may be one of the channels of the BLE transmission protocol. It should be noted that disclosed embodiments also applicable to other types of low energy communication protocols.

Figure 6:
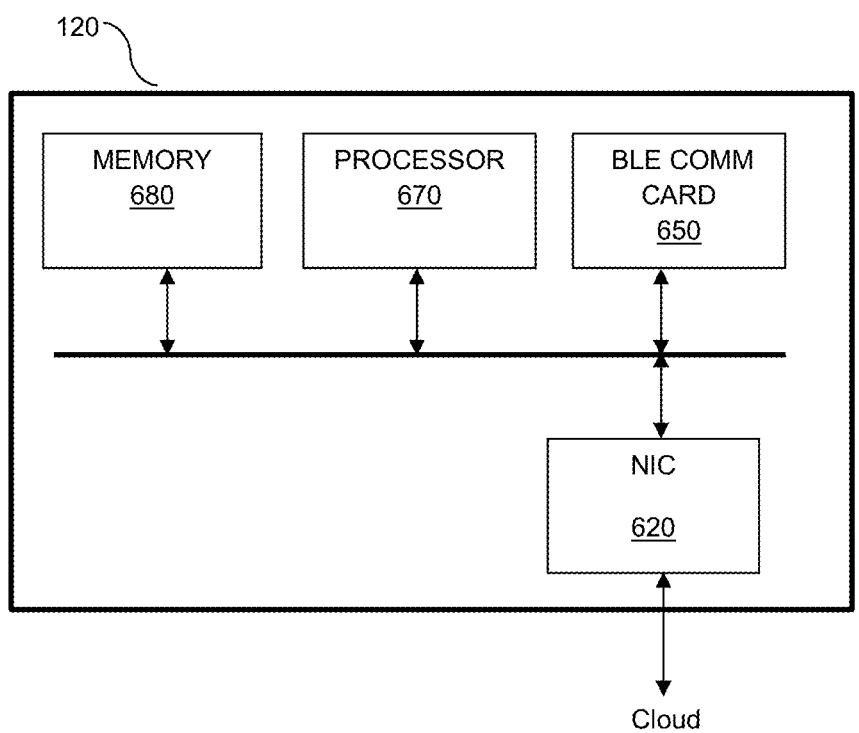
FIG. 6 is a circuit diagram of a gateway used for detecting a material using low energy sensing, according to an embodiment.

In an embodiment, the ID is a unique identifier (ID) of the IoT tag 110 which is set during production of the IoT tag 110. The data packets sent by the IoT tag 110 are received at the gateway 120, which in turn, periodically sends the data packets to the server 140. An example block diagram of the gateway 120 is shown in FIG. 6. In an embodiment, the gateway 120 may be installed with an agent or application (not shown in FIG. 1). The agent, when executed, is configured to control the communication between the IoT tag 110 and the server 140. The agent is also configured to receive an interference event caused by the placement of a container proximate to the IoT tag 110. Such an event is received by the server 140 and displayed as notification on a display. For example, a glass of yogurt is placed proximate to the IoT tag 110, then a notification including information about the yogurt will be displayed.

The server 140 is configured to process the data packets received by the gateway 120 in order to detect an interference event for each of the IoT tag 110. An interference event may be indicative of, for example, proximity, i.e., an object is within the IoT tag 110's proximity that has not been there before; surface characteristics, i.e., there is something about the surface of the a container 150 detected within the IoT tag 110's proximity; orientation, (i.e., the container 150 detected within the IoT tag 110's proximity may have a certain orientation relative to the IoT tag 110); temperature change, i.e., there is a change in temperature within the IoT tag 110's proximity.

In an embodiment, the detection of an interference event is based on analysis of the digital frequency words. That is, if any change was determined respective of previously received word, this is an indication that a container placed proximate to the respective IoT tag 110 was changed. The difference value between two consecutive received words can indicate on the type of change. The analysis is performed using machine learning processes performed by the server 140. These processes or techniques are discussed in greater below.

In the alternative, detection of RF values from multiple co-located IoT tags 110 may be analyzed within various temporal windows to determine which of the respective frequency words have anomalies. Co-location sensing may be detected by the gateway 120. When no container is present, the IoT tags 110 may have similarly sensed RF values.

In an example embodiment, upon detection of an interference event, an interference notification is sent from the server 140 to the gateway 120. The interference notification may include an ID of the respective IoT tag 110 and information to be displayed.

Figure 2:
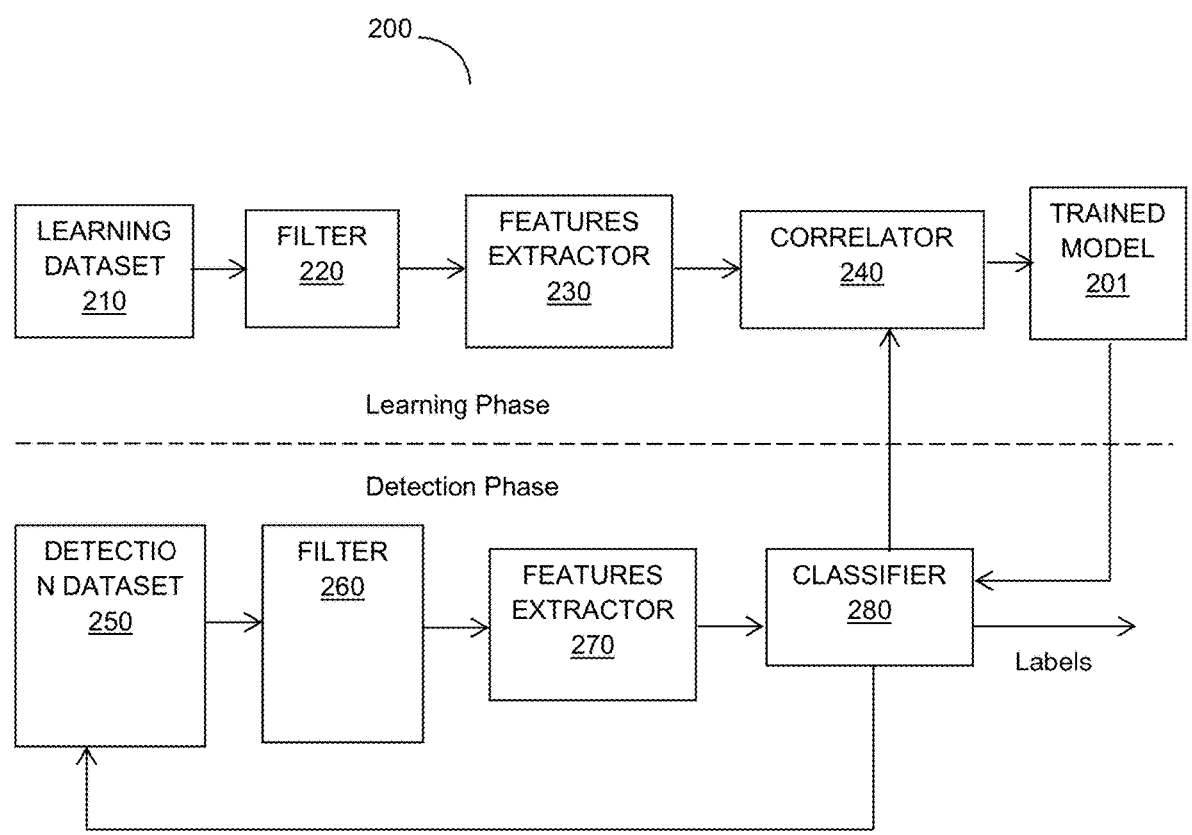
FIG. 2 is a flow diagram illustrating a training phase for a supervised model utilized for detecting a material, according to an embodiment.

FIG. 2 is a schematic diagram of a machine learning framework 200 utilized to detect material type in a container equipped with the IoT tag and the level of contents of the material in a container. The level of contents may be binary (empty or full) or a percentage volume of the material in the container. The framework 200 can be further configured to detect the type of surface that the container is placed on. For the sake of simplicity and without limitation on the disclosed embodiments, FIG. 2 will be discussed also with reference to the elements shown in FIG. 1.

The supervised machine learning framework 200 operates in two phases: learning and detection. In the learning phase, a trained model 201 is generated and trained, while in the detection phase, the trained model 201 is utilized for identification of the type of contents of the container 150. The trained model 201, in an embodiment, is generated and trained using semi-supervised machine learning techniques.

In the learning phase, are packets which include frequency words received from the IoT tags 110. Such received words are aggregated and saved as a learning dataset 210. The aggregation of frequency words may be for a predefined time window (e.g., all words during an hour-time window) or per IoT tag ID.

The learning dataset 210 is input to a filter 220 configured to filter out "noisy" readings of the frequency words. The filter 220 may be implemented using a boundary decision technique, outlier detection, and the like. In an embodiment, upon filtering noisy readings, the forwarding of information of the filtered noise is propagated. Such information can be further analyzed by the feature's extractor, such that eventually the trained model refers also to a noise level which can be different with respect to different material (e.g., air may gain more noise than condensed material).

The filtered words are fed into a features extractor 230 configured to generate a set of features representing an interface event. Depending on the material make-up or such of the container 150, the value of the frequency word may vary. By modeling the values of the frequency words, and attributing the values to specific materials, the material make-up of the container 150 may be identified. In an example, a noise level of received frequency word may be one of the extracted features. That is, upon filtering, information of on the filtered noise is fed into the features extractor 270, such that eventually the train model refers also to noise level which can be different with respect to different material (e.g., air may gain more noise than condensed material).

In an embodiment, the set of features include at least one feature. The feature extraction may include computing a value of frequency word or words using, for example, a Fast Fourier transform (FFT), delta values between two consecutive frequency words, and the like. The feature extraction may father consider the proximity between IoT tags based on co-located group of tags.

The extracted features (values of frequency words) are fed to the correlator 240. In an embodiment, the correlator 240 implements a semi-supervised machine learning algorithm for analyzing the features and generating, using external supporting data, a trained model 201. Examples for the semi-supervised machine learning algorithm includes, and/or based on, decision trees, label propagation, local outlier factor, isolation forest, and the like.

The supporting data includes labels of certain features previously identified as a specific type of material, information as when the learning dataset was gathered. For example, when the learning dataset was gathered at a room at certain temperature, an empty room, crowded room, and the like.

The trained model, generated by the correlator 240, is used to map or correlate unseen frequency words (features) to labels indicating the type of material in the container 150 or the surface of the container 150. The unseen frequency words are analyzed during the detection phase. The trained model 201 can also be trained to label the rate at which the frequency words are received. Such rate can be labeled to indicate a level of material within the container. A high transmission rate frequency words would be level as empty container, while a low transmission rate frequency words would be level as full. The values of "high" and "low" and the values in between are trained.

According to an embodiment the trained model 201 is generated when the IoT tags are at rest and at a controlled environment (e.g., a lab). It should be noted that the trained model 201 may be generated and trained based on information received from a plurality of co-located IoT tags.

In an embodiment, during the detection phase, frequency words received from the gateway 120 are aggregated and saved as a detection dataset 250. The aggregation is performed over a predefined detection time window or per tag ID.

The detection dataset 250 is input to the filter 260 that performs the filtration process with the filter 260. The filtered frequency words are fed to features extractor 270. The feature extraction may include computing a value of frequency word or words using, for example, a FFT, delta values between two consecutive frequency words, statistical information, and the like.

The set of features (values of frequency words) are fed to the classifier 280. The classifier 280 is configured to label the values of the frequency words identify the type of material in a container. Further, the classifier 280 may be configured to determine the level of the material in the container. The labeling is based on the trained model 201 and the set features vector of the respective IoT tag.

The classifier 280 can be implemented using known classifying techniques utilized in supervised or semi-supervised machine learning. For example, the classifier 280 can be implemented using techniques that spread the semi-supervised to supervised range. Examples for such techniques include a k-means, a gaussian mixture model (GMM), a random forest, manifold learning, decision trees, and the like. In an embodiment, the labels provided by the classifier 280 may be fed into the correlator 240 to improve or otherwise update the trained model 201. In yet another embodiment, the labels provided by the classifier 280 may be fed to the detection dataset for labeling input words.

In an example embodiment, the correlator 240 and/or the classifier 280 can be realized by one or more hardware logic components utilized to process artificial intelligence (AI) tasks, such as a digital signal processor (DSP), a tensor processing unit, or other AI accelerators.

The datasets 210 and 250 can be stored in a memory, which can be volatile (e.g., RAM, etc.) memory, non-volatile (e.g., ROM, flash memory, etc.) memory, or a combination thereof. Alternatively, or collectively, the datasets 210 and 250 can be stored in a storage, or any other medium which can be used to store the desired information.

The machine learning framework 200 discussed herein can be trained to detect other interference events, such as proximity to a container including an IoT tag, motion of the IoT tag, orientation of a container including IoT tag, location of a container including an IoT tag, and temperature changes in material in a container including the IoT tag, in temperature within such IoT tag proximity.

Figure 3A:
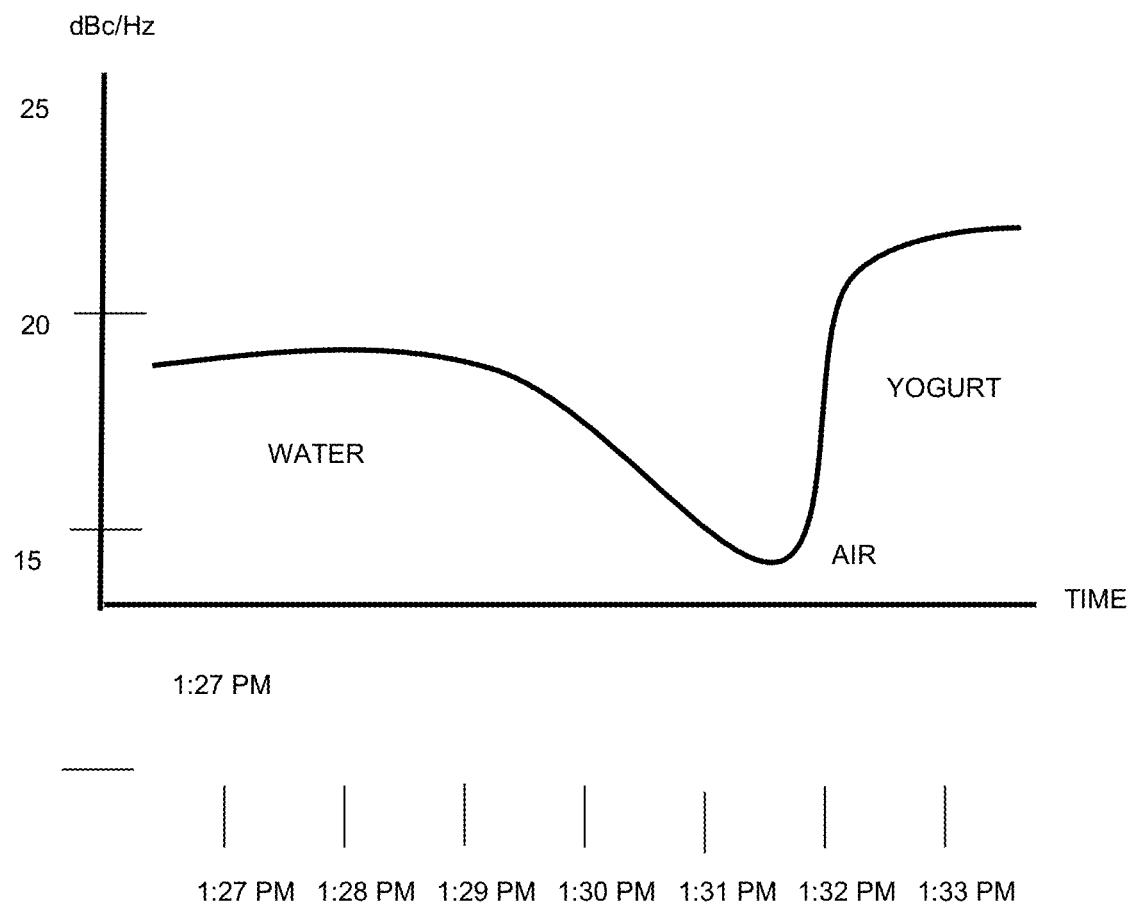
FIG. 3A is a graph showing a frequency word telemetry corresponding to labeled items in the container, according to an embodiment.

FIG. 3A is an example graph of frequency word telemetry corresponding to labeled items in the container, according to an embodiment. Various items such as water, air, and yogurt were put in the container 150 and placed near one of the IoT tags 110 over time. During the training phase, a learning dataset 210 resulting from the measured disturbances proximate a particular IoT tag 110 with values that reflect the different contents of the container 150 are labeled as one of the identified materials based on the method described in FIG. 2.

As an example, a frequency word of approximately 18 dBC/Hz may be labeled as water; frequency word of approximately 15 dBC/Hz may be labeled as air; and frequency word frequency word of about 23 dBC/Hz may be labeled as yogurt during the training process. The dBC unit is decibels relative to the carrier, i.e., the power ratio of a signal to a carrier signal, expressed in decibels. Over time, with repeated collection of frequency words, the trained model 201 may be developed using semi-supervised machine learning described in FIG. 2. Afterwards, the trained model 201 may be applied during the detection phase to identify the material of the content in the container 150 as one of water, air, or yogurt, based on the frequency word values measured, and the results may be fed back to the correlator 240 to improve the trained model 201 over time.

Figure 3B:
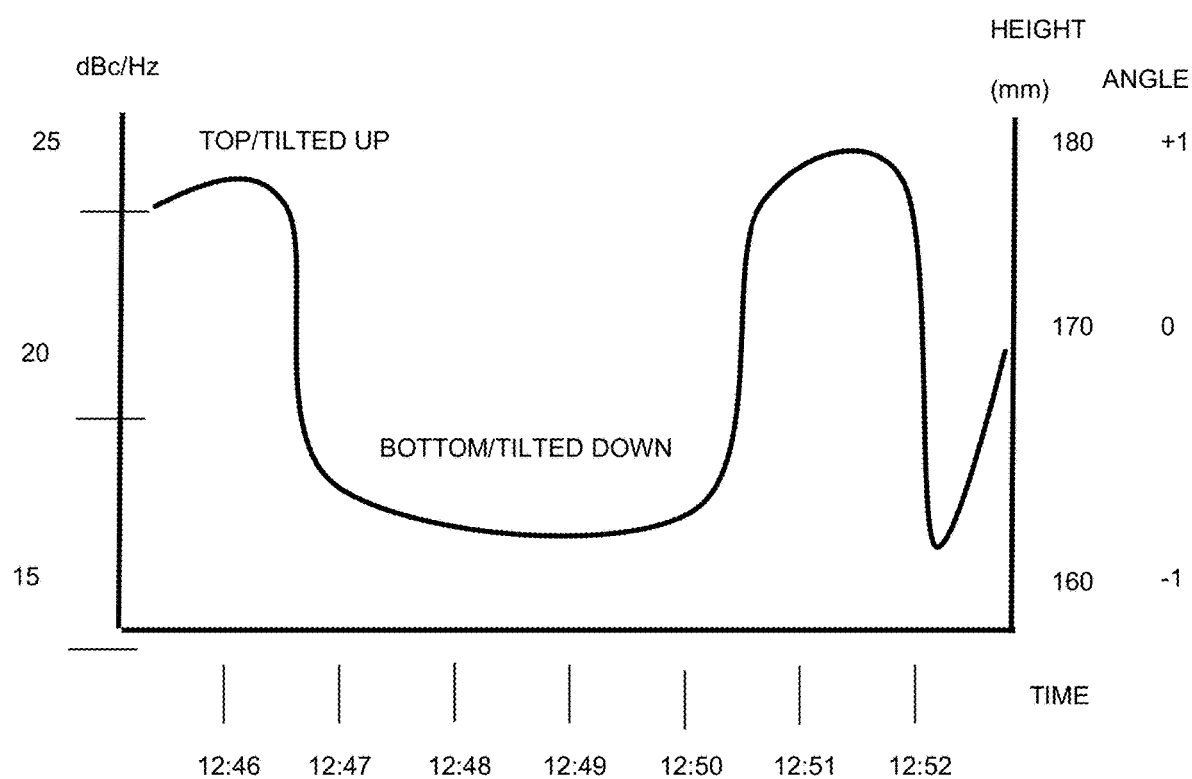
FIG. 3B is a graph frequency word telemetry corresponding to the surface and orientation detection, according to an embodiment.

FIG. 3B is an example graph of frequency word telemetry corresponding to the surface and orientation detection, according to an embodiment. For example, depending on where the IoT tag 110 is placed relative to the container 150 (e.g., at the top or bottom of the container 150 at different height level, the detected frequency word value may vary). A trained model 201 may be constructed during the training phase as described in FIG. 2. Then, in the detection phase, additional detection dataset 250 may be classified as a certain surface (i.e., top surface or bottom surface).

That is, in an embodiment, during the training phase, a learning dataset 210 resulting from the measured disturbances proximate a particular IoT tag 110 with values that reflect the different contents of the container 150 are labeled as one of the identified surface (i.e., top surface, middle surface, bottom surface) based on the method described in FIG. 2. As an example, frequency word of approximately 24 dBC/Hz may be labeled as top surface, while frequency word of approximately 16 dBC/Hz may be labeled as bottom surface during the training process.

Over time, with repeated collection of frequency words, the trained model 201 may be developed using semi-supervised machine learning described in FIG. 2. Afterwards, the trained model 201 may be applied during the detection phase to identify the surface detected as one of top, middle, or bottom of the container 150, based on the frequency word values measured, and the results may be fed back to the correlator 240 to improve the trained model 201 over time.

Alternatively, using similar concepts in semi-supervised modeling and applying the model identifying dataset as a particular label, orientation of the container 150 may further be identified. During the training phase, a learning dataset 210 resulting from the measured disturbances proximate a particular IoT tag with values that reflect the angular orientation of the container 150 are labeled as one of the identified orientation relative to a reference plane based on the method described in FIG. 2. As an example, a frequency word of approximately 24 dBC/Hz may be labeled as "tilted up"; while frequency word of approximately 16 dBC/Hz may be labeled as "tilted down" during the training process.

Over time, with repeated collection of frequency words, the trained model 201 may be developed using semi-supervised machine learning described in FIG. 2. Afterwards, the trained model 201 may be applied during the detection phase to identify the orientation of the container 150 as being tilted up or down based on the frequency word values measured, and the results may be fed back to the correlator 240 to improve the trained model 201 over time.

Figure 4:
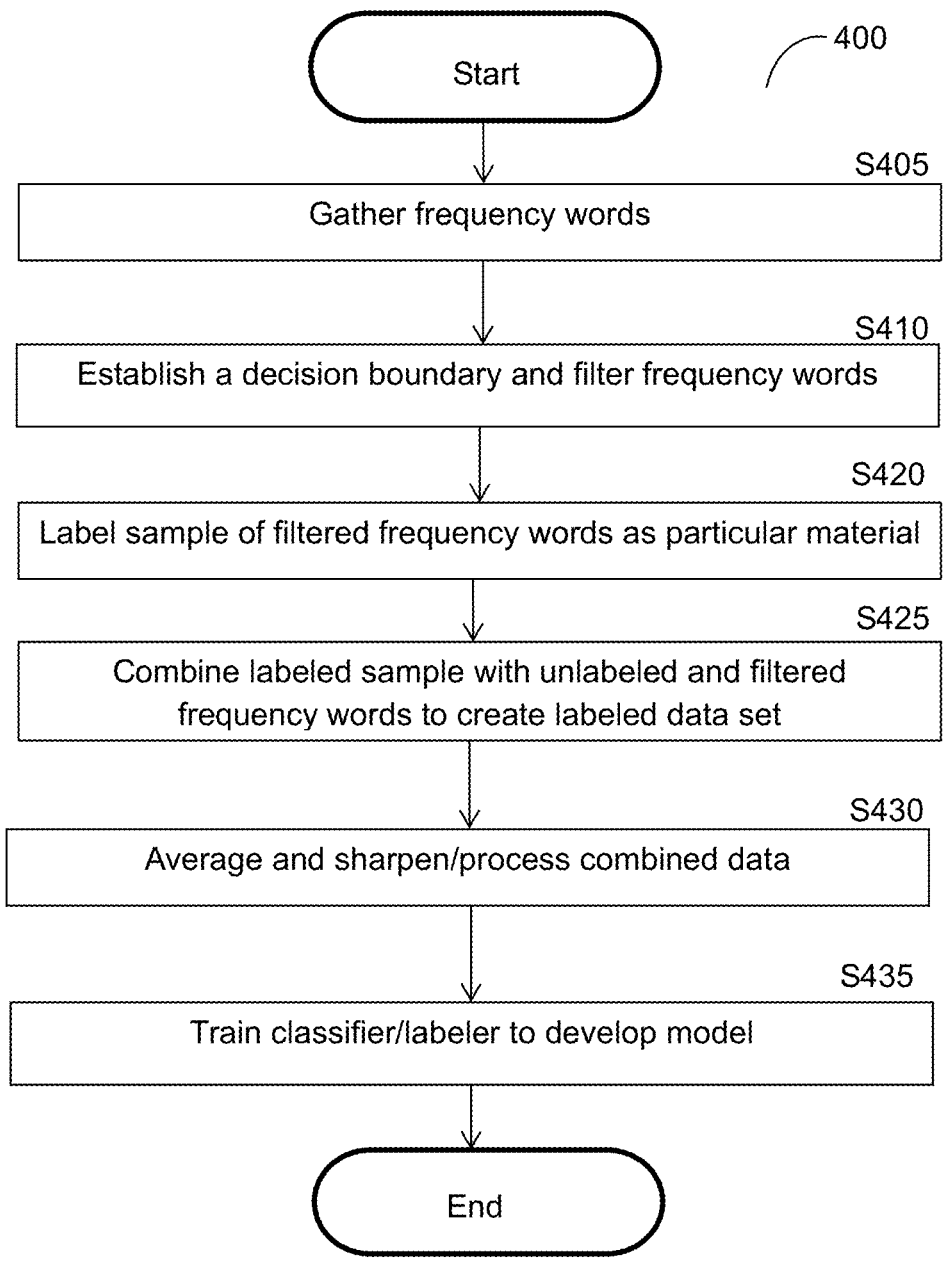
FIG. 4 is a flowchart for a method of training a model for detecting a material, according to an embodiment.

FIG. 4 is an example flowchart 400 for a method of training a model for detecting a material type in a container, according to an embodiment. At S405, a plurality of frequency words gathered from measurements by the IoT tag 110 and transmitted by the gateway 120 is received. Then, at S410, the plurality of frequency words is filtered based on an established decision boundary, or filter, to retain the frequency words that are outside of the defined boundary, or outliers where interference to the low energy field where the tag is considered to be at rest is detected.

At S420, a sample of the filtered frequency words is obtained, and each of the sample of the filtered frequency words is labeled as a particular material associated with the sample. Once all of the samples of the filtered frequency words are labeled, the method proceeds to S425, where the labeled and filtered frequency words are recombined with the unlabeled and filtered frequency words to create a labeled data set. At S430, the combined data further processed, and is averaged and sharpened by a semi-supervised algorithm or a supervised algorithm. At S435, a model for identifying a material based on the detected frequency word is developed, based on the combined and processed data including the labeled and unlabeled frequency words.

Figure 5:
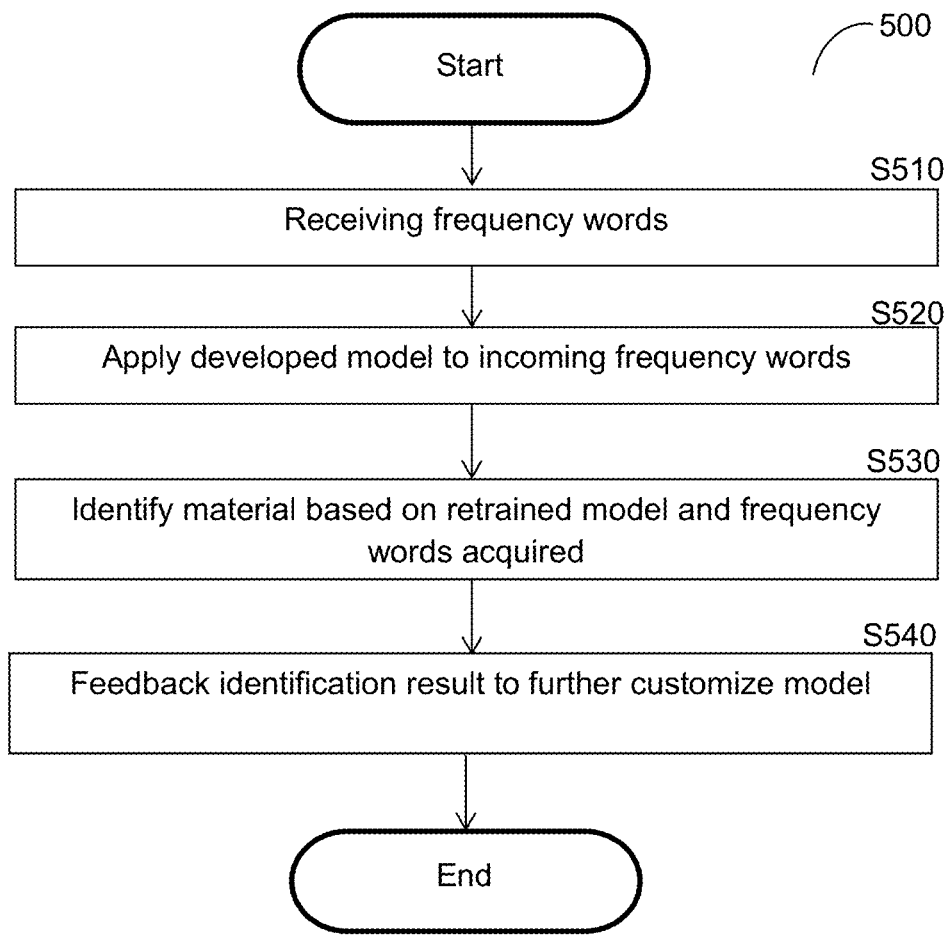
FIG. 5 is a flowchart of a method for detecting a material in a container using low energy sensing, according to an embodiment.

FIG. 5 is an example flowchart 500 of a method for detecting a type of material using low energy sensing, according to an embodiment. At S510, a frequency word is received. This frequency word may be based on the frequency words gathered at S405, or may be based on new signals detected by the IoT tag 110.

At S520, a model previously trained is applied to the received frequency words, and based on the model, the material that corresponds to the received frequency word is identified under S530. As described previously with regard to FIG. 4, the model is developed based on a combination of a labeled sample of frequency word that is filtered based on an established decision boundary, and an unlabeled frequency word that is filtered based on the established decision boundary described at S425.

At S540, the result of the material identification is fed back, so the model may be further adjusted and customized to more accurately identify material corresponding to the frequency word detected.

It should be appreciated that since existing BLE low energy, already widely used for data transmission among devices, is used, according to the disclosed embodiments, for detecting material inside the container 150, there is no need to use various expensive equipment incompatible with low energy modality to detect material make-up of the container 150. Also, since the IoT tag 110 is battery less, low energy consumption is achieved.

In an embodiment, the methods described above with regard to FIGS. 2-5 may be applied to detect a surface of the container 150, or the orientation of the surface of the container 150 with reference to the IoT tag 110 in proximity with the container 150. That is, once the material makeup of the container 150 has been identified based on the model developed for the particular material, additional semi-supervised training may be performed based on method described above to further refine the model to account for different orientations of the container 150 made of that particular model, and then apply the new models in a similar fashion as determined in FIGS. 3 and 5 to determine both the surface and orientation characteristics of the container 150 relative to the IoT tag 110.

It should be noted that the type of material of the surface and contents of the container depends on the orientation of the IoT tag 110. Specifically, when IoT is placed on the bottom of an object pointing downwards, such that signals can be used to classify the material on which it stands (surface detection). Alternatively, placing the IoT tag on a container pointing inwards, would allow to detect the type of contents of the container and the material from which the container is made.

FIG. 6 is an example diagram of the gateway 120 includes a BLE communication card 650 and a network interface card (NIC) 620, the BLE card 650 communicates with the IoT tag 110 over a BLE network (not shown), while the NIC 620 allows communication with the server 140 over the Internet (not shown), or other type of network.

In an embodiment, the gateway 120 may be installed with an agent or application executed by the processor 670 and stored in the memory 680. The agent, when executed, is configured to control the communication with the IoT tag 110 and the server 140. The agent is also configured to receive an interference event caused by the placement of a container proximate to the IoT tag 110. Such an event is received by the server 140 and displayed as notification on a display. For example, a glass of yogurt is placed proximate the IoT tag 110, then a notification including information about the yogurt will be displayed.

It should be noted that processor 670 may be realized as one or more hardware logic components and circuits. For example, and without limitation, illustrative types of hardware logic components that can be used include field programmable gate arrays (FPGAs), application-specific integrated circuits (ASICs), Application-specific standard products (ASSPs), system-on-a-chip systems (SOCs), general-purpose microprocessors, microcontrollers, digital signal processors (DSPs), and the like, or any other hardware logic components that can perform calculations or other manipulations of information.

The memory 680 may be volatile (e.g., RAM, etc.), non-volatile (e.g., ROM, flash memory, etc.), or a combination thereof. The agent (or application) are realized in software. Software shall be construed broadly to mean any type of instructions, whether referred to as software, firmware, middleware, microcode, hardware description language, or otherwise. Instructions may include code (e.g., in source code format, binary code format, executable code format, or any other suitable format of code). The instructions, when executed by the processor 670, cause the execution of the agent over the processor 670.

Figure 7:
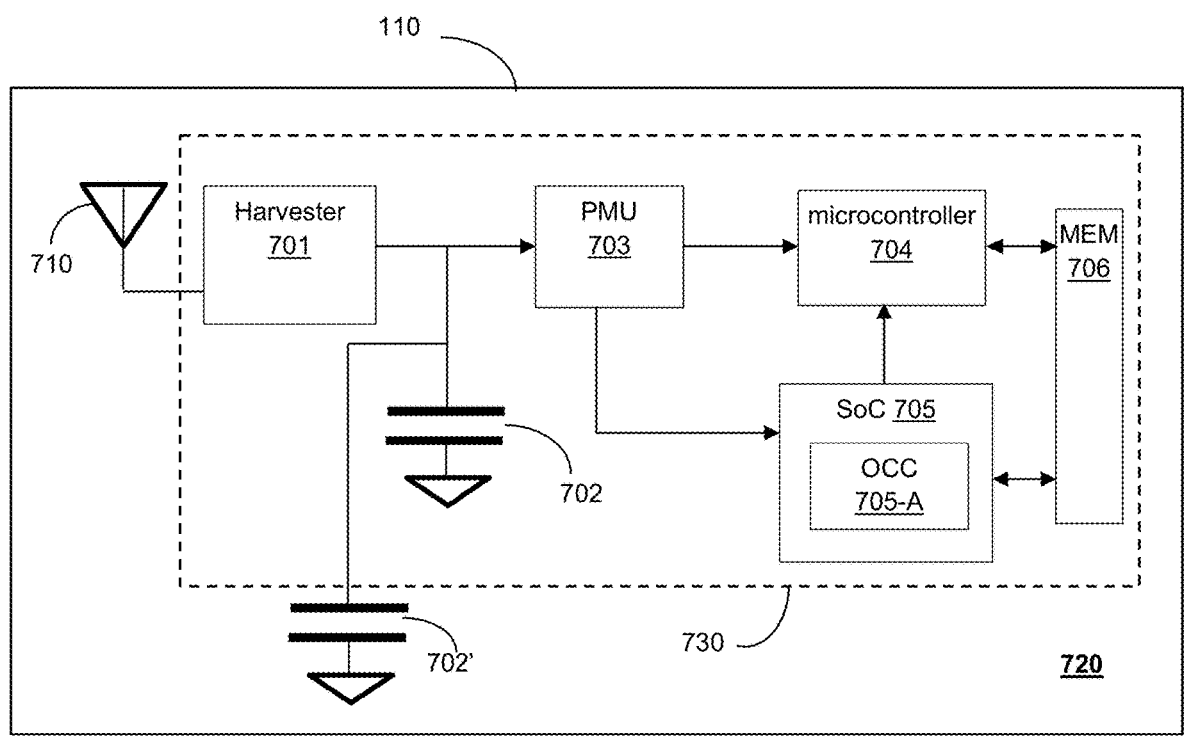
FIG. 7 is a schematic diagram of a wireless device, designed according to the disclosed embodiments.

FIG. 7 shows an example schematic diagram of an IoT tag 110, designed according to the disclosed embodiments. The form factor of the IoT tag 110 is an on-die package-less. The IoT tag 110, as schematically demonstrated in FIG. 7, includes an energy harvester 701, coupled to an on-die capacitor 702 and an external passive capacitor 702', a power management unit (PMU) 703, a microcontroller 704, a system on chip (SoC) 705, and a retention memory 706. The IoT tag 110 further may include at least one antenna 710 glued to a substrate 720, for example. In another embodiment, the antenna 710 may be printed on the substrate or etched to the substrate. In a further embodiment a passive external capacitor may take the place of the antenna 710. In an embodiment, the substrate 720 is made of a low-cost material, such as, but not limited to, polyethylene (PET), polyimide (PI), and polystyrene (PS). In another embodiment, the substrate 720's pattern (layout) can be any of aluminum, copper, or silver. The glue utilized to glue to die and/or antenna 710 may be include materials such as an anisotropic conductive film (ACP), any type of conductive glue, solder past, and the like.

In the embodiment shown in FIG. 7, the antenna 710 is coupled to the harvester 701 and may be utilized for energy harvesting as well as wireless communication. In some embodiments, multiple antennas may be utilized to harvest energy at multiple frequency bands. Other embodiments may include one or more antenna for energy harvesting and an antenna to receive/transmit wireless signals at the BLE frequency band.

The SoC 705 includes a number of execution functions realized as analog circuits, digital circuits, or both. Examples for such execution functions are provided below. The SoC 705 is also configured to carry out processes independently or under the control of the microcontroller 704. Each process carried out by the SoC 705 also has a state, and processes can communicate with other processes through an IPC protocol. In the configuration illustrated in FIG. 7, the SoC 705 and/or the microcontroller 704 loads the context of processes and reads data from the retention memory 706.

The SoC 705 is partitioned into multiple power domains. Each power domain is a collection of gates powered by the same power and ground supply. To reduce the power consumption, only one power domain is turned on during execution. The SoC 705 can perform functions, such as reading from and writing to memory, e.g., of peripherals and can execute simple logic operations; tracking power level of the SoC 705; generating and preparing data packets for transmission; cyclic redundancy check (CRC) code generation; packet whitening; encrypting/decrypting and authentication of packets; converting data from parallel to serial; and staging the packet bits to the analog transmitter path for transmission.

In a preferred embodiment, the SoC 705 includes an oscillator calibration circuit (OCC) 705-A. The OCC 705-A includes at least one frequency locking circuit (FLC), each of which is coupled to an oscillator (both are not shown). The FLC calibrates the frequency of an oscillator using an over-the-air reference signal. In an embodiment, the calibration of the respective oscillator is performed immediately prior to a data transmission session and remains free running during the data transmission session. The FLC can be realized using frequency locked loop (FLL), a phased locked loop (PLL), and a delay locked loop (DLL). An example implementation of an oscillator calibration circuit 705-A is discussed in U.S. patent application Ser. No. 15/994,388 to Yehezkely, assigned to the common assignee.

According to the disclosed embodiments, the energy harvester 701, the capacitor 702, PMU 703, microcontroller 704, SoC 705, and retention memory 706 are integrated in a die 730. The die 730 is glued to the substrate 720. The IoT tag 110 does not include any external DC power source, such as a battery.

In an embodiment, the microcontroller 704 implements electronic circuits (such as, memory, logic, RF, etc.) performing various functions allowing communication using a low energy (power) communication protocol. Examples for such a protocol includes, but are not limited to, Bluetooth®, LoRa, Wi-Gi®, nRF, DECT®, Zigbee®, Z-Wave, EnOcean, and the like. In a preferred embodiment, the microcontroller 704 operates using a Bluetooth Low energy (BLE) communication protocol.

In some embodiments, the microcontroller 704 is integrated with wireless sensors (not shown) to a complete an IoT device functionality.

The harvester 701 is configured to provide multiple voltage levels to the microcontroller 704, while maintaining a low loading DC dissipation value. In an example implementation, the energy harvester 701 may include a voltage multiplier coupled to the antenna 710. The voltage multiplier may be a Dickson multiplier, while the antenna is a 710 receive/transmit antenna of the microcontroller 704. That is, in such a configuration, the antenna is primarily designed to receive and/or transmit wireless signals according to the respective communication protocol of the low-energy IoT tag 110 (e.g., 2.400-2.4835 GHz signal for BLE communication).

It should be noted that the antenna 710 may also be designed for energy harvesting and may operate on a different frequency band, direction, or both, than those defined in the standard of the respective communication protocol. Regardless of the configuration, energy can be harvested from any wireless signals received over the air. Alternatively, energy can be harvested from any other sources, such as solar, piezoelectric signals, and the like.

The harvested energy is stored in the on-die capacitor 702 and/or the external capacitor 702'. The PMU 703 is coupled to the capacitor 702 and is configured to regulate the power to the microcontroller 704 and SoC 705. Specifically, as the capacitance of the capacitor 702 is very limited, the power consumption should be carefully maintained. This maintenance is performed to avoid draining of the capacitor 702, thus resetting the microcontroller 704. The PMU 703 can be realized using a Schmitt trigger that operates on a predefined threshold (Vref), e.g., Vref=0.85V.

In another embodiment, the PMU 703 may be further configured to provide multi-level voltage level indications to the microcontroller 704. Such indications allow the microcontroller 704 to determine the state of a voltage supply at any given moment when the capacitor 702 charges or discharges. According to this embodiment, the PMU 703 may include a detection circuitry controlled by a controller. The detection circuitry includes different voltage reference threshold detectors, where only a subset of such detectors is active at a given time to perform the detection.

The IoT tag 110 does not include any crystal oscillator providing a reference clock signal. According to an embodiment, the reference clock signal is generated using over-the-air signals received from the antenna 710. As noted above, in a typical deployment, a free running oscillator is locked via a Phase-Locked Loop (PLL) to a clock, originating from a crystal oscillator. According to the disclosed embodiments, the OCC 705-A calibrates the frequency of an oscillator using an over-the-air reference signal. The oscillator(s) implemented in the tag 730 are on-die oscillators and may be realized as a Digitally Controlled Oscillator (DCO).

The retention memory 706 is a centralized area that is constantly powered. Data to be retained during low power states is located in the retention memory 706. In an embodiment, the retention area is optimized to subthreshold or near threshold voltage, e.g., 0.3V-0.4V. This allows for the reduction of the leakage of the retention cells.

Figure 8:
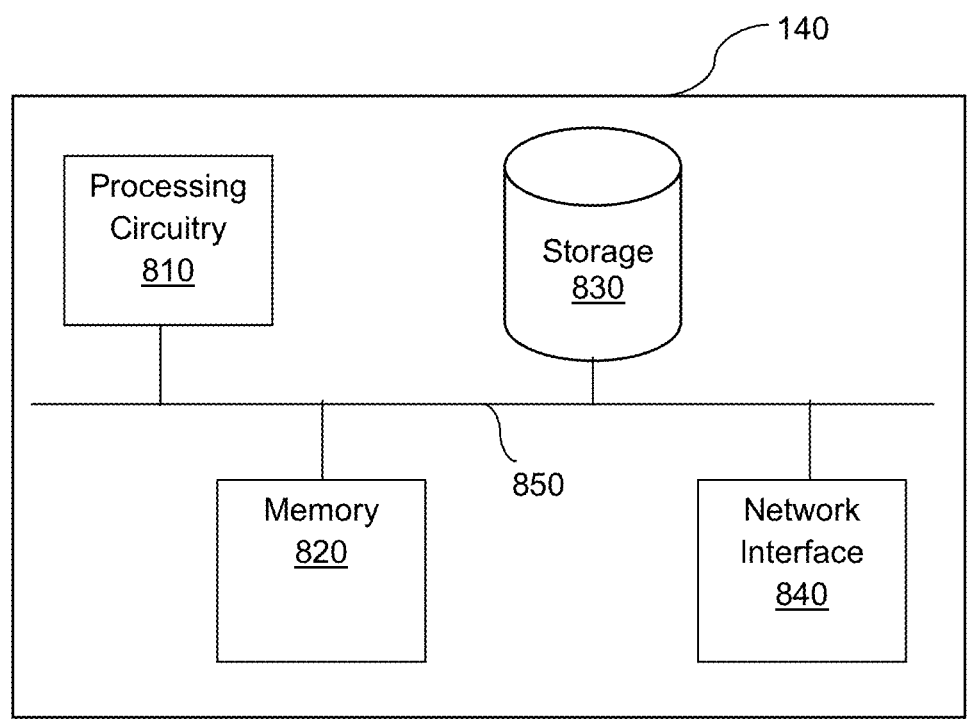
FIG. 8 is a schematic diagram of a server according to an embodiment.

FIG. 8 is an example schematic diagram of a server 140 according to an embodiment. The server 140 includes a processing circuitry 810 coupled to a memory 820, a storage 830, and a network interface 840. In an embodiment, the components of the server 140 may be communicatively connected via a bus 850.

The processing circuitry 810 may be realized as one or more hardware logic components and circuits. For example, and without limitation, illustrative types of hardware logic components that can be used include field programmable gate arrays (FPGAs), application-specific integrated circuits (ASICs), Application-specific standard products (ASSPs), system-on-a-chip systems (SOCs), general-purpose microprocessors, microcontrollers, digital signal processors (DSPs), and the like, or any other hardware logic components that can perform calculations or other manipulations of information.

The memory 820 may be volatile (e.g., RAM, etc.), non-volatile (e.g., ROM, flash memory, etc.), or a combination thereof. In one configuration, computer readable instructions to implement one or more embodiments disclosed herein may be stored in the storage 830.

In another embodiment, the memory 820 is configured to store software. Software shall be construed broadly to mean any type of instructions, whether referred to as software, firmware, middleware, microcode, hardware description language, or otherwise. Instructions may include code (e.g., in source code format, binary code format, executable code format, or any other suitable format of code). The instructions, when executed by the processing circuitry 810, cause the processing circuitry 810 to perform the various processes described herein.

The storage 830 may be magnetic storage, optical storage, and the like, and may be realized, for example, as flash memory or other memory technology, CD-ROM, Digital Versatile Disks (DVDs), or any other medium which can be used to store the desired information.

The network interface 840 allows the server 140 to communicate with the gateway 120 for the purpose of, for example, receiving data, sending data, and the like. Further, the network interface 840 allows the server 140 to communicate with the IoT tag 110 for the purpose of collecting frequency words.

It should be understood that the embodiments described herein are not limited to the specific architecture illustrated in FIG. 8, and other architectures may be equally used without departing from the scope of the disclosed embodiments.

The various embodiments disclosed herein can be implemented as hardware, firmware, software, or any combination thereof. Moreover, the software is preferably implemented as an application program tangibly embodied on a program storage unit or computer readable medium consisting of parts, or of certain devices and/or a combination of devices. The application program may be uploaded to, and executed by, a machine comprising any suitable architecture. Preferably, the machine is implemented on a computer platform having hardware such as one or more central processing units ("CPUs"), a memory, and input/output interfaces. The computer platform may also include an operating system and microinstruction code. The various processes and functions described herein may be either part of the microinstruction code or part of the application program, or any combination thereof, which may be executed by a CPU, whether or not such a computer or processor is explicitly shown. In addition, various other peripheral units may be connected to the computer platform such as an additional data storage unit and a printing unit. Furthermore, a non-transitory computer readable medium is any computer readable medium except for a transitory propagating signal.

All examples and conditional language recited herein are intended for pedagogical purposes to aid the reader in understanding the principles of the disclosed embodiment and the concepts contributed by the inventor to furthering the art, and are to be construed as being without limitation to such specifically recited examples and conditions. Moreover, all statements herein reciting principles, aspects, and embodiments of the disclosed embodiments, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

It should be understood that any reference to an element herein using a designation such as "first," "second," and so forth does not generally limit the quantity or order of those elements. Rather, these designations are generally used herein as a convenient method of distinguishing between two or more elements or instances of an element. Thus, a reference to first and second elements does not mean that only two elements may be employed there or that the first element must precede the second element in some manner. Also, unless stated otherwise, a set of elements comprises one or more elements.

As used herein, the phrase "at least one of" followed by a listing of items means that any of the listed items can be utilized individually, or any combination of two or more of the listed items can be utilized. For example, if a system is described as including "at least one of A, B, and C," the system can include A alone; B alone; C alone; 2A; 2B; 2C; 3A; A and B in combination; B and C in combination; A and C in combination; A, B, and C in combination; 2A and C in combination; A, 3B, and 2C in combination; and the like.

What is claimed is:

1. A method for detecting material type using low-energy sensing, comprising:

receiving frequency words from a tag attached to a container containing material, wherein the tag provides a low-energy sensing configured to transmit the frequency words, wherein each frequency word is based on a frequency calibration of the tag with respect to a currently specified transmission frequency for transmission of data by the tag;

extracting at least a first data feature from the received frequency words, wherein the extracted at least a first data feature changes in response to a type of material in the container;

classifying the extracted at least a first data feature to label a type of the material in the container, wherein the classifying is performed by a trained machine classifier that employs a trained machine learning model; and sending a notification indicating the type of material in the container as classified by the trained machine classifier.

2. The method of claim 1, wherein a frequency word changes when the tag is out of a calibration with respect to the currently specified transmission frequency for transmission of data by the tag.

3. The method of claim 1, wherein each received frequency word is measured as dBC/Hz, wherein the dBC is dBC unit is decibels relative to a carrier frequency.

4. The method of claim 1, further comprising:

extracting a second data feature from the received frequency words, wherein the second data feature is a rate of reception of frequency words.

5. The method of claim 4, further comprising:

classifying the second data feature to label a level of the material in the container, wherein the classifying of the second data feature is performed by the trained machine classifier.

6. The method of claim 1, further comprising:

training the trained machine classifier to label unseen frequency words.

7. The method of claim 6, wherein training the trained machine classifier further comprises:

receiving a learning dataset of unseen frequency words;

filtering frequency words demonstrating at least abnormal readings;

extracting data features from the filtered frequency words; and training the trained machine learning model based on the extracted data features, wherein the trained machine learning model is trained to at least label materials based on an extracted at least a first data feature.

8. The method of claim 7, wherein the trained machine learning model is any one of: a supervised model and an unsupervised model.

9. The method of claim 1, wherein the frequency words are transmitted over a Bluetooth Low Energy (BLE) protocol.

10. The method of claim 1, wherein tag is a battery-less internet of things (IoT) tag.

11. The method of claim 1, wherein the trained machine classifier is implemented as hardware logic adapted as an artificial intelligence processor.

12. A non-transitory computer readable medium having stored thereon instructions for causing a processing circuitry to execute a process for detecting material type using low-energy sensing, the process comprising:

receiving frequency words from a tag attached to a container containing material, wherein the tag provides a low-energy sensing configured to transmit the frequency words, wherein each frequency word is based on a frequency calibration of the tag with respect to a currently specified transmission frequency for transmission of data by the tag, wherein a frequency word changes when the tag is out of a calibration with respect to the currently specified transmission frequency for transmission of data by the tag;

extracting at least a first data feature from the received frequency words, wherein the extracted at least a first data feature changes in response to a type of material in the container;

classifying the extracted at least a first data feature to label a type of the material in the container, wherein the classifying is performed by a trained machine classifier that employs a trained machine learning model; and sending a notification indicating the type of material in the container as classified by the trained machine classifier.

13. A system for developing a treatment plan using multi-stage machine learning, comprising:

a processing circuitry; and a memory, the memory containing instructions that, when executed by the processing circuitry, configure the system to:

receive frequency words from a tag attached to a container containing material, wherein the tag provides a low-energy sensing configured to transmit the frequency words, wherein each frequency word is based on a frequency calibration of the tag with respect to a currently specified transmission frequency for transmission of data by the tag;

extract at least a first data feature from the received frequency words, wherein the extracted at least a first data feature changes in response to a type of material in the container;

classify the extracted at least a first data feature to label a type of the material in the container, wherein the classifying is performed by a trained machine classifier that employs a trained machine learning model; and send a notification indicating the type of material in the container as classified by the trained machine classifier.

14. The system of claim 13, wherein a frequency word changes when the tag is out of a calibration with respect to the currently specified transmission frequency for transmission of data by the tag.

15. The system of claim 13, wherein each received frequency word is measured as dBC/Hz, wherein the dBC is dBC unit is decibels relative to a carrier frequency.

16. The system of claim 13, wherein the system is further configured to:

extract a second data feature from the received frequency words, wherein the second data feature is a rate of reception of frequency words.

17. The system of claim 16, wherein the system is further configured to:

classify the second data feature to label a level of the material in the container wherein the classifying of the second data feature is performed by the trained machine classifier.

18. The system of claim 13, wherein the system is further configured to:

train the trained machine classifier to label unseen frequency words.

19. The system of claim 18, wherein the system is further configured to:

receive a learning dataset of unseen frequency words;

filter frequency words demonstrating at least abnormal readings;

extract data features from the filtered frequency words; and train the trained machine learning model based on the extracted data features, wherein the machine learning model is trained to at least label materials based on an extracted at least a first data feature.

20. The system of claim 19, wherein the machine learning model is any one of: a supervised model and an unsupervised model.

21. The system of claim 13, wherein the frequency words are transmitted over a Bluetooth Low Energy (BLE) protocol.

22. The system of claim 13, wherein tag is a battery-less internet of things (IoT) tag.

23. The system of claim 13, wherein the trained machine classifier is implemented as hardware logic adapted as an artificial intelligence processor.

* * * * *